United States Patent [19]

Mittleman et al.

[11] 4,038,983
[45] Aug. 2, 1977

[54] FLUID INFUSION PUMP

[75] Inventors: Herbert Mittleman, Deerfield; Ricky Robert Ruschke, Wheeling, both of Ill.

[73] Assignee: Baxter Travenol Laboratories, Inc., Deerfield, Ill.

[21] Appl. No.: 652,938

[22] Filed: Jan. 26, 1976

[51] Int. Cl.² ............................................. A61M 5/14
[52] U.S. Cl. ........................ 128/214 C; 128/232; 417/435; 417/478
[58] Field of Search .......... 128/214 R, 214 C, 214 F, 128/214.2, 231, 232, 350 V; 251/4, 125, 342; 417/435, 478

[56] References Cited

U.S. PATENT DOCUMENTS

| 2,907,325 | 10/1959 | Burke | 128/214 C |
|---|---|---|---|
| 2,989,052 | 6/1961 | Broman | 128/214 C |
| 3,521,635 | 7/1970 | Koehn | 128/214 C |
| 3,654,932 | 4/1972 | Newkirk | 128/350 V |
| 3,664,339 | 5/1972 | Santomieri | 128/214 C |
| 3,965,925 | 6/1976 | Gooch | 251/342 X |

FOREIGN PATENT DOCUMENTS

| 1,235,482 | 5/1960 | France | 128/214 C |
|---|---|---|---|
| 23,507 of | 1898 | United Kingdom | 251/4 |

Primary Examiner—Dalton L. Truluck
Attorney, Agent, or Firm—Eugene M. Cummings; Paul C. Flattery

[57] ABSTRACT

A flow system for infusing a fluid such as blood from a storage reservoir into the human body includes a hand-operated pump for increasing the flow rate of the fluid through the system when required. The pump includes a duckbill-type valve assembly user-conditionable to an open position wherein fluid can pass freely through the valve and air trapped in the housing of the pump can be purged upline to the reservoir, and to a closed position wherein reverse flow of fluid in the system is prevented during operation of the pump.

12 Claims, 13 Drawing Figures

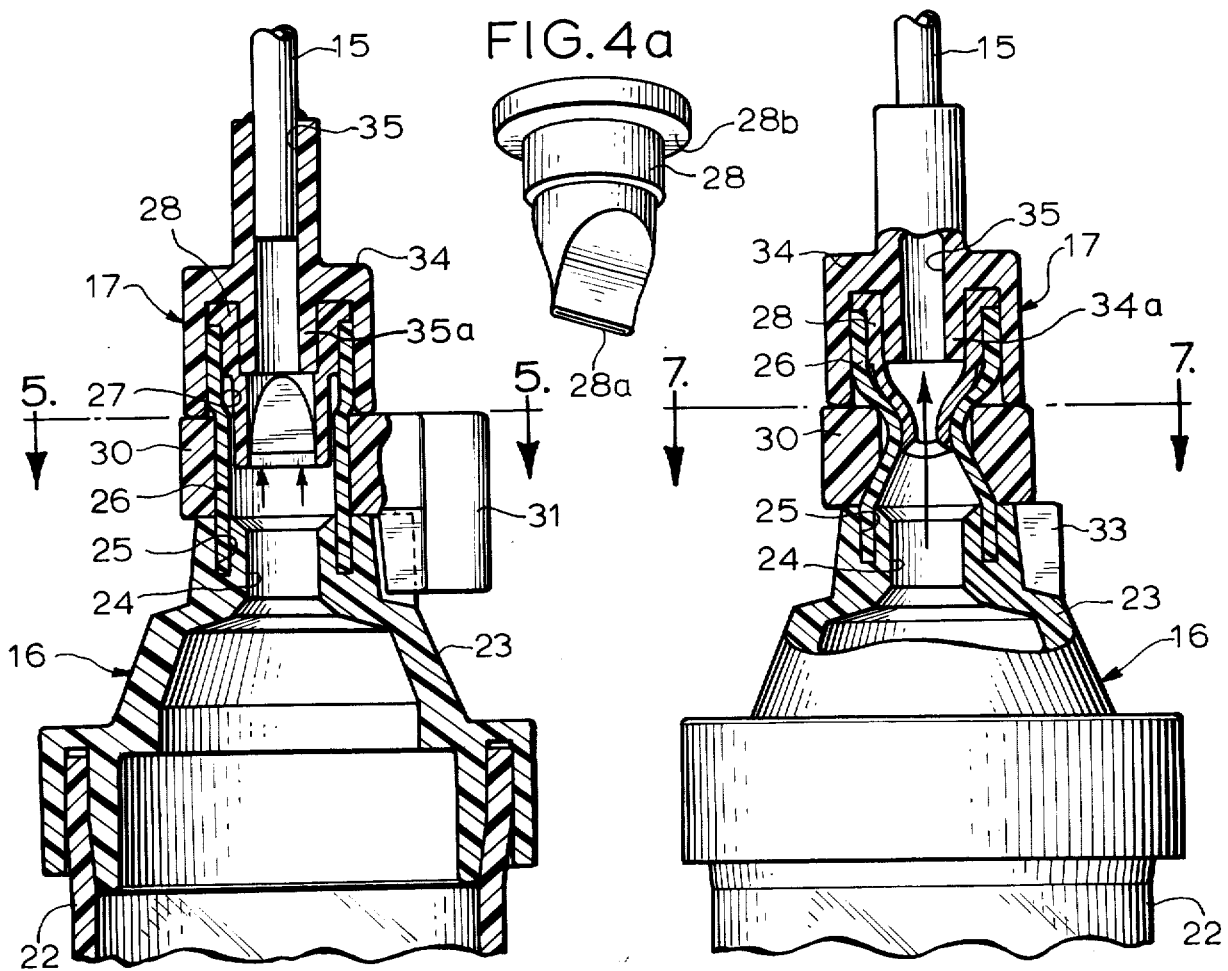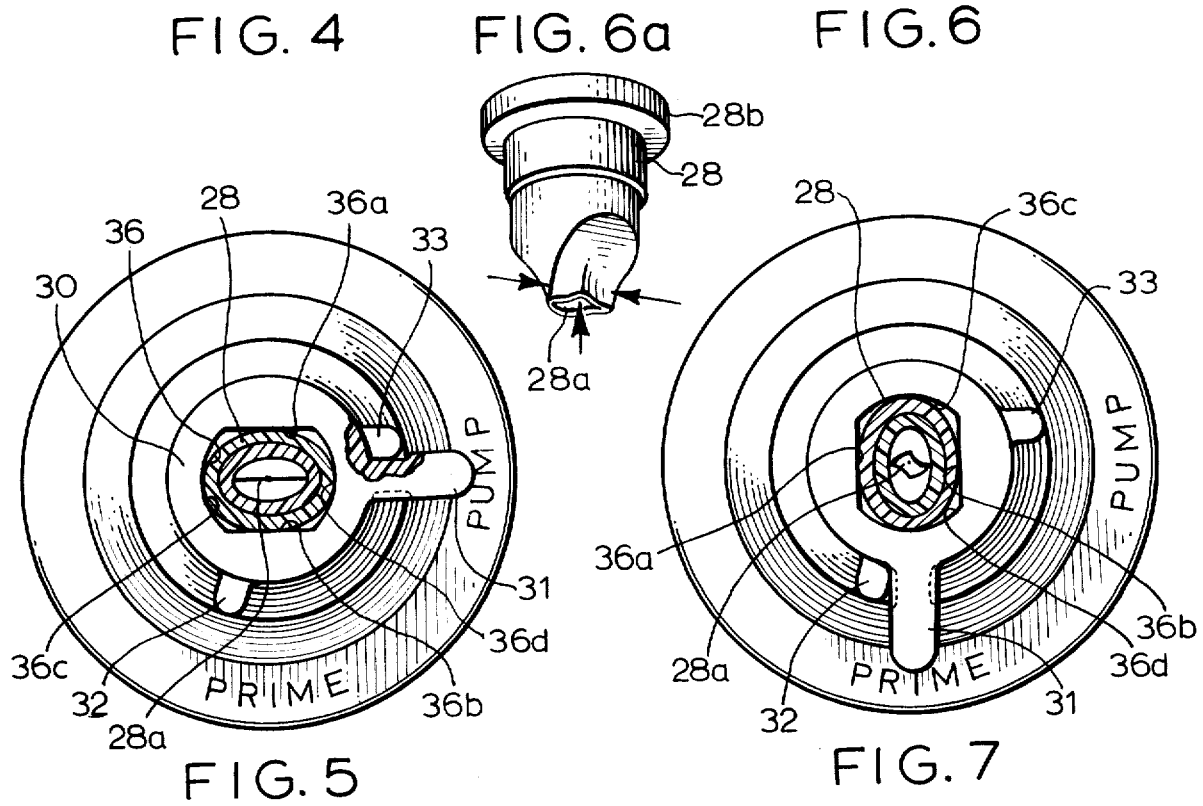

ized pump, indicated generally by reference numeral 16. From pump 16 fluid is directed by additional tubing 17 to a hypodermic needle 18 for infusion into the patient.

FLUID INFUSION PUMP

BACKGROUND OF THE INVENTION

The present invention relates generally to systems for administering fluids to the human body, and more particularly to an improved manually-operable pressure pump for use in such systems.

During the infusion of fluids such as blood into the human body it is frequently desirable that the flow rate of the fluid be temporarily increased beyond its normal gravity flow rate. This is particularly so in emergency situations wherein large quantities of fluid must be infused in a short period of time. Such increased flow rates are most conveniently obtained by means of a hand pump disposed in the flow path of the administration set being used to transport fluid into the vein or artery. As conditions require, the attending physician or technician manually actuates the hand pump, causing a quantity of fluid to be infused with each such actuation.

Hand operated pumps heretofore provided in fluid administration sets have not provided entirely satisfactory operation in that they have been difficult to purge of air or other separated gases which may accumulate and coalesce within the pump chamber. Such gases not only decrease the capacity of the pump, but also increase the danger that an air embolus may be accidentally infused into the patient. Both the ball-type and diaphragm-type check valves commonly used in prior art pumps allowed the pumps to be purged only with great difficulty by deforming the housing of the valve and forcing the ball or diaphragm valve away from its valve seat so as to establish an air path to the reservoir. This operation required the expenditure of much time and care on the part of medical personnel. Furthermore, such prior art ball- and diaphragm-type check valves did not allow completely free passage of the fluid in gravity-feed situations since they included no provision for being conditioned to a completely open state.

Accordingly, it is a general object of the present invention to provide a new and improved pressure pump for use in a fluid infusion system.

It is another object of the present invention to provide a new and improved pressure pump from which air and other separated gases can be more easily purged.

It is another object of the present invention to provide a new and improved manually-operated pump for use in a fluid infusion system which includes a valve which can be conditioned to a purge position wherein air trapped within the pump can be purged, or to a pump position wherein fluid can be forced down line into the body.

It is another object of the present invention to provide a manually-operated pump having a user-conditionable valve which automatically protects against inadvertent misconditioning by the user.

It is another object of the present invention to provide an in line manually actuated pump for a fluid infusion system which can be conditioned to provide no hindrance to the free flow of fluid through the system.

SUMMARY OF THE INVENTION

The invention is directed, in a flow system for infusing fluid into the human body, to a pressure pump which includes a pump housing defining a chamber for the pump and an inlet passageway extending to the chamber. Means including a valve insert member are disposed within the passageway for controlling fluid flow through the passageway, and useractuable valve control means are provided for selectively deforming the valve insert member to open the insert member whereby trapped air can be purged from the chamber through the passageway.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjuction with the accompanying drawings, in the several figures of which like reference numerals identify like elements, and in which:

FIG. 4 is an enlarged cross-sectional view of the valve assembly of the pump taken along line 4—4 of FIG. 3 showing the valve assembly in its closed or pump position.

FIG. 4a is an enlarged perspective view of the duckbill valve insert utilized in the pump valve assembly shown in FIG. 4.

FIG. 5 is an enlarged cross-sectional view of the pump valve assembly taken along line 5—5 of FIG. 4.

FIG. 6 is an enlarged cross-sectional view of the valve assembly similar to FIG. 4 showing the valve assembly in its open or prime position.

FIG. 6a is an enlarged perspective view of the duckbill valve insert utilized in the pump valve assembly shown in FIG. 6.

FIG. 7 is an enlarged cross-sectional view of the pump valve assembly taken along line 7—7 of FIG. 6.

DESCRIPTION OF THE PREFERRED EMBODIMENT

Figure 1:
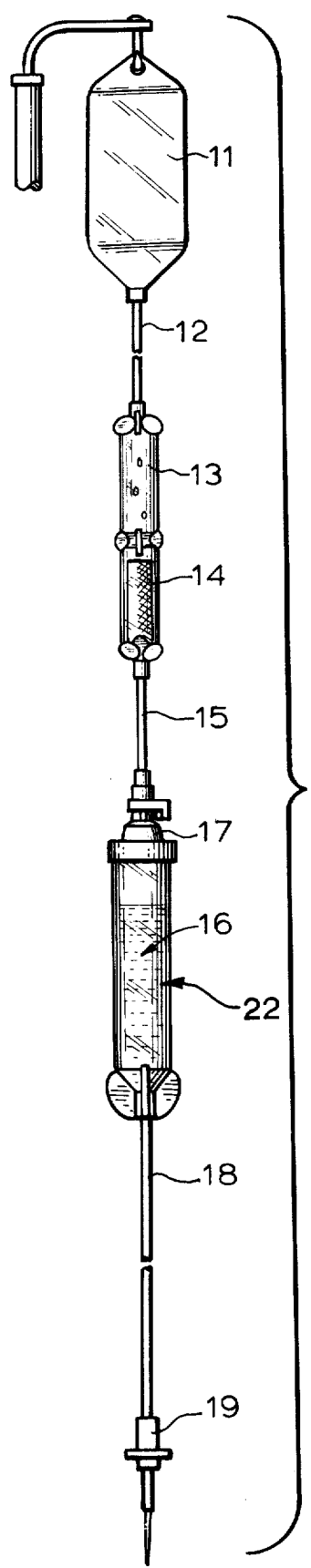
FIG. 1 is a perspective view of a blood infusion system incorporating a manually-operated pump constructed in accordance with the invention.

Referring to the Figures, and particularly to FIG. 1, a fluid infusion set 10 constructed in accordance with the invention is connected to a reservoir 11 in which a quantity of fluid to be infused is contained. The reservoir 11 empties into a tubing 12 which connects with a drip chamber 13 of conventional design and construction wherein the flow of blood from the reservoir can be observed. The drip chamber empties into a filter 14 also of conventional design and construction wherein clots and other impurities are removed from the fluid.

Filtered fluid from filter 14 is conveyed by a flexible tubing segment 15 to the input of an inline user-actuated pump 16. The purpose of this pump is to increase the flow rate of the system when required, and to this end the pump may include a flexible-walled housing 22 defining a user-compressible pump chamber and a valve assembly 17 for preventing reverse flow in the system when the pump is actuated. The output of pump 16 is connected by a flexible tubing segment 18 to a needle adaptor 19 to which a needle of appropriate size and shape is connected for insertion into a vein or artery. The infusion set 10 may be constructed of plastic and packaged in a sealed sterile and nonpyrogenic condition so as to be available for immediate use.

Figure 2:
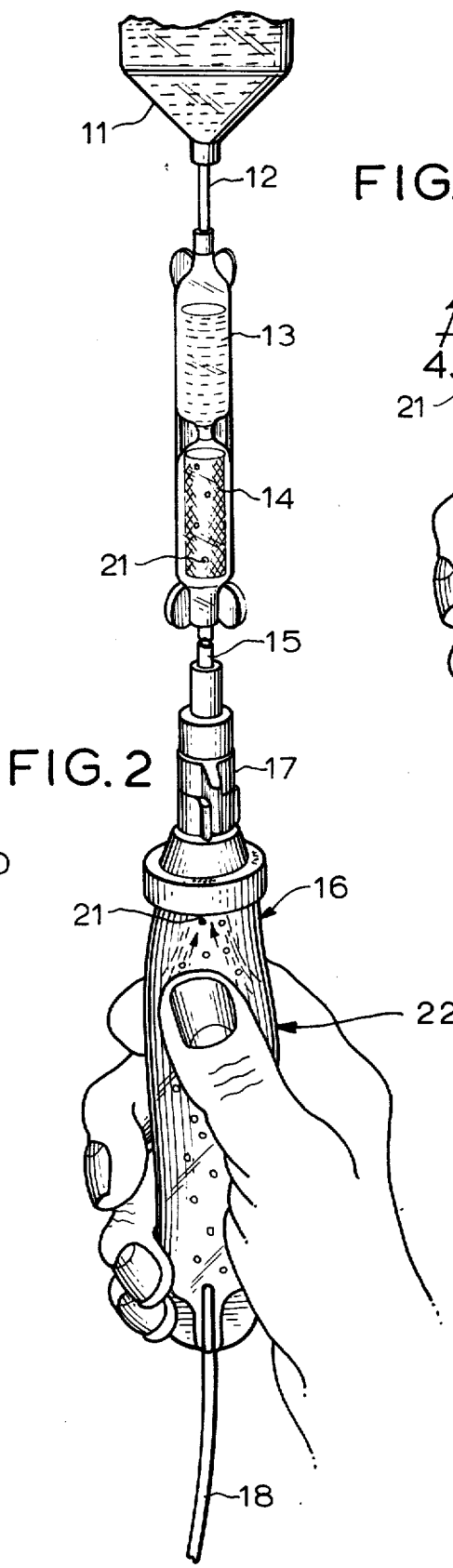
FIG. 2 is an enlarged perspective view of a portion of the blood infusion system showing air being purged from the pump chamber.
Figure 3:
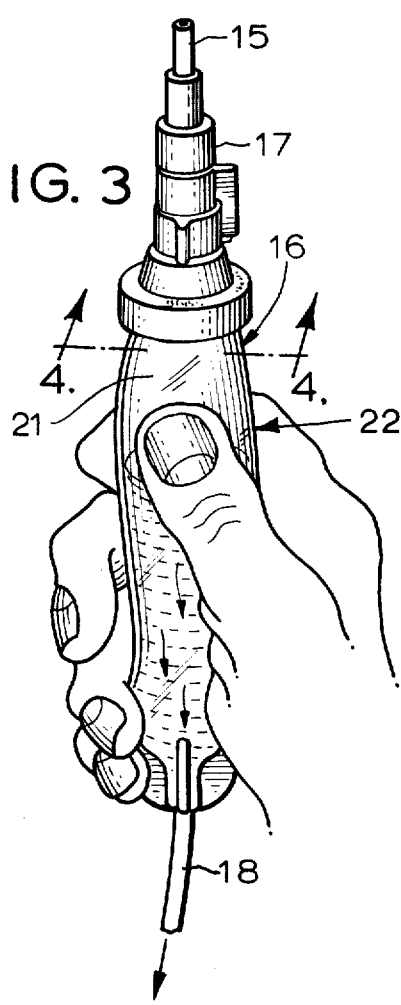
FIG. 3 is an enlarged perspective view of the manually-operated pump portion of the infusion system showing the pump in operation pumping blood through the system.
Figure 8:
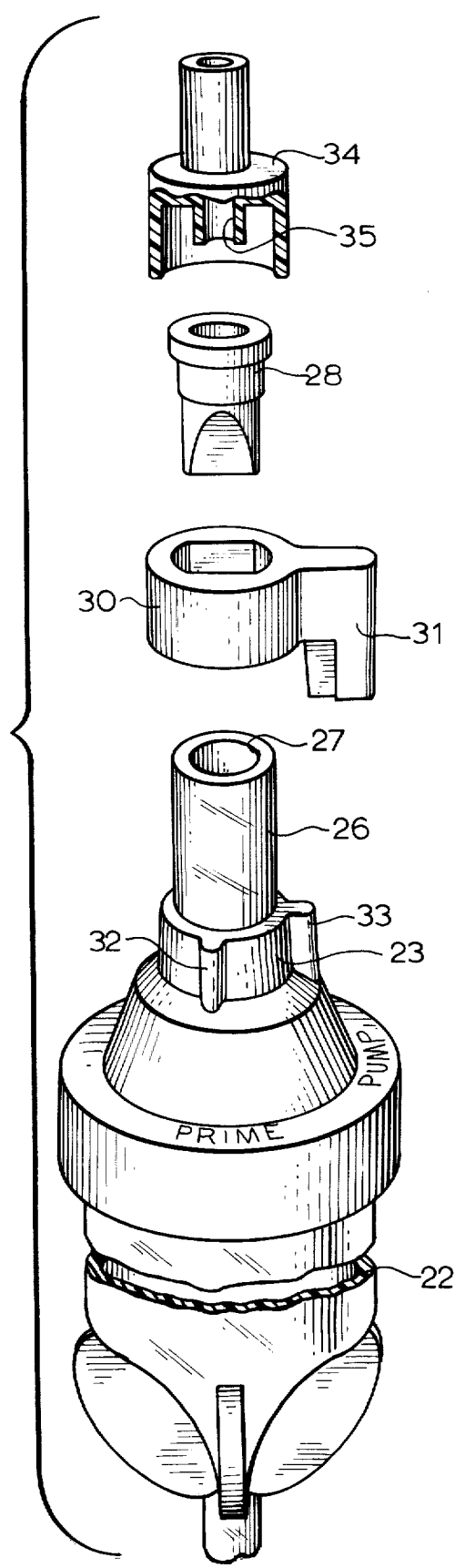
FIG. 8 is an enlarged exploded perspective view partially in cross-section showing the principal components of the pump valve assembly.

Referring to FIG. 2, to eliminate air pockets which may be formed within the pump housing the pump includes, in accordance with the invention, a valve assembly 17. This assembly can be conditioned by the user to an open or PRIME mode, wherein air trapped in the pump as bubbles 21 can be forced upline to the fluid reservoir 11 by squeezing the pump housing 22. After this purging operation has been completed, the valve assembly 17 can be conditioned to a closed or PUMP mode, as shown in FIG. 3 wherein it functions as a check valve to allow fluid to enter but not leave the pump through tubing segment 15 as the pump housing 22 is squeezed.

Referring to FIGS. 4-8, the pump housing 22 is generally cylindrical in form and is formed of a flexible transparent plastic material which can be squeezed by the user to force fluid from the interior of the housing. The bottom end of the housing is pinched together around tubing 18 and heat sealed to form a pressure-tight seal. The top end of the housing is fitted with a cap 23 which may be molded of plastic or other suitable material.

Referring to FIG. 4, the top end of the pump housing is fitted with an end cap 23 which includes an axially-aligned inlet aperture 24 for establishing fluid communication with the pump chamber. End cap 23 also includes a coaxial ring-shaped channel 25 into which a deformable sleeve 26 of relatively thick plastic may be fitted to provide support means for the other components of the valve assembly. A duckbill-type valve insert member 28 having a diametric valve slit 28a is positioned within sleeve 26 and held in position along the axis thereof by means of a flange 28b at its open end.

To provide means by which the user can selectively open valve insert 28 for the purpose of purging air from the pump housing the valve assembly 17 includes a valve actuator collar 30 slidably mounted over sleeve 26. Collar 30 includes a tab 31 which allows the user to rotate the collar approximately 90° around sleeve 26 between two tab stops 32 and 33 (FIG. 8) integrally molded into end cap 23. Collar 30 and valve insert 28 are retained in position by means of the valve cap 34 fitted over the open end of sleeve 26. Valve cap 34 includes a central downwardly-projecting hub portion 34a (FIG. 6) through which an aperture 35 is provided in axial alignment with valve assembly 28 and aperture 24 for establishing fluid communication with tubing segment 15. The hub portion 34a extends into the interior of valve insert 28 to prevent the insert from collapsing under the compression force of collar 30.

Referring to FIG. 5, the valve actuator collar 30 includes a four-sided aperture 36 having tow opposing flat walls 36a and 36b and two opposing curved walls 36c and 36d. When the collar is positioned in its PUMP position as shown in FIGS. 4 and 5 the flat walls 36a and 36b are aligned parallel to the valve slit 28a of the duckbill valve insert 28. With this alignment the cross section of aperture 36 conforms to the oval cross section of the valve insert and no force is exerted by the walls on the valve insert. As a result the valve insert remains in its closed or PUMP position as shown in FIG. 4a and the valve functions as a check valve.

When the valve actuator collar 30 is rotated clockwise (as viewed from above) to its PRIME position, as shown in FIGS. 6 and 7, the flat walls 36a and 36b of aperture 36 are aligned perpendicularly to valve slit 28a and bear against the sides of the valve insert to open the valve slits 28a, as shown in FIG. 6a. This allows trapped air to exit from the pump housing as previously described in connection with FIG. 2. Also, in this position the valve provides no hindrance to the free flow of fluid through the system since the opening through the valve slit 28a is larger than the lumen of the tubing. This is an important advantage where the system is utilized primarily for gravity-flow infusion. In a typical application the tubing may have a lumen of 0.133 inch diameter and the valve slit 28a may have a diameter of approximately 0.200 inch in its open or purge condition.

Figure 9:
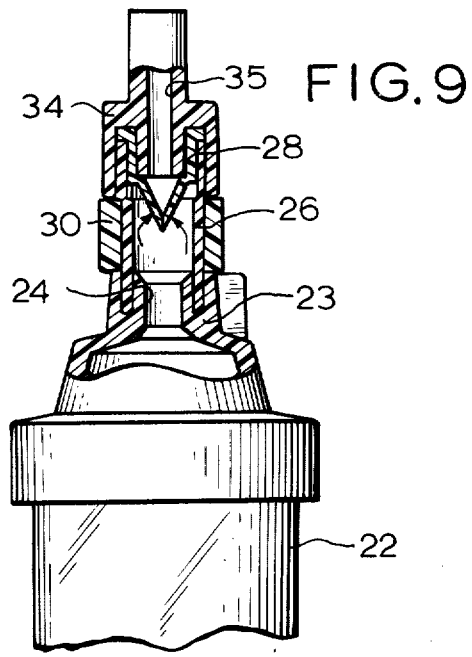
FIG. 9 is a cross-sectional view of the pump valve assembly in its open or prime position illustrating automatic closing of the valve upon inadvertent actuation of the pump.

Should the user attempt to pump fluid through the system with the valve assembly set in its PRIME position the back pressure exerted by the fluid will force the duckbill valve closed, as shown in FIG. 9. This is an important safety feature since it ensures that blood will be delivered under pressure when required notwithstanding the positioning of the valve assembly.

Figure 10:
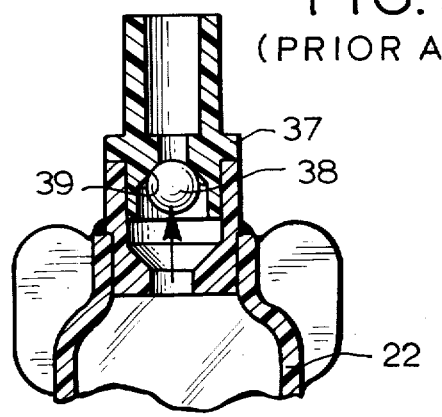
FIG. 10 is a cross-sectional view of a typical prior art ball-type check valve assembly.
Figure 11:
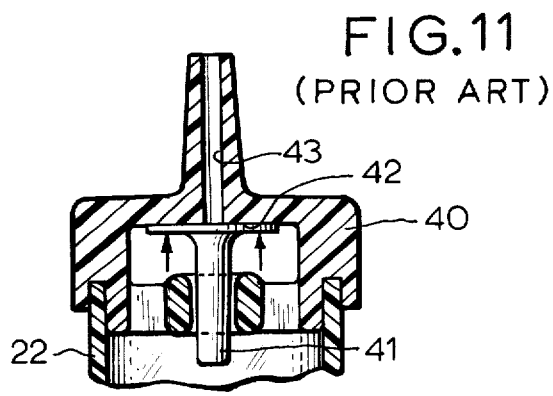
FIG. 11 is a cross-sectional view of a typical prior art diaphragm-type check valve assembly.

Thus, unlike the valve assemblies utilized with prior art pump assemblies, valve assembly 17 can be selectively conditioned by the user to an open position to permit purging of the pump, or to a closed position to operate as a check valve for infusing blood under pressure into a patient. In prior art valve assemblies, such as the ball-type check valve shown in FIG. 10, the purging function could be obtained only by distorting the valve housing 37 sufficiently to force the ball 38 away from its valve seat 39. Similarly, in the prior art diaphragm-type check valve shown in FIG. 11 it was necessary to distort the valve housing 40 to a sufficient extent to force the diaphragm plunger 41 away from its valve seat 42.

Thus, an infusion system has been shown and described which can be quickly and easily connected for dispensing a fluid such as blood from reservoirs of conventional design and construction. The system includes a novel inline pressure pump which enables the user to increase the flow rate of the fluid when required by the patient's condition. The pump assembly included a duckbill-type valve which can be selectively conditioned by the user to an open position to permit fluid to flow freely through the pump and trapped air within the pump chamber to be purged, or to a closed position wherein the valve assembly operates as a conventional check valve to cause the pump to force fluid into the patient. As an added safety feature the valve assembly automatically closes to allow normal pumping action should the pump assembly be inadvertently actuated with the valve assembly conditioned in its open or purge position.

While a particular embodiment of the invention has been shown and described, it will be obvious to those skilled in the art that changes and modifications may be made without out departing from the invention in its broader aspects, and, therefore, the aim in the appended claims is to cover all such changes and modifications as fall within the true spirit and scope of the invention.

We claim:

1. In a flow system for infusing fluid into the human body, a pressure pump comprising, in combination:
   a pump housing defining a chamber for said pump and an inlet passageway extending to said chamber;
   means including a valve insert member disposed in said passageway for controlling fluid flow through said passageway; and
   user-actuable valve control means for selectively deforming said valve insert member to open said insert member, said valve control means and said valve insert means cooperating to enable the purging of trapped air from said chamber through said inlet passageway.

2. A flow system as defined in claim 1 wherein said valve insert member comprises a duckbill-type valve.

3. A flow system as defined in claim 2 wherein said duckbill valve is radially deformed by said valve control means.

4. A flow system as defined in claim 1 wherein said valve control means comprise a ring-shaped collar member mounted for rotation about said valve insert member.

5. A flow system as defined in claim 4 wherein said valve control collar has an aperture disposed around said valve insert member, and said valve insert member and said collar aperture are out-of-round in cross-section whereby said valve insert is radially compressed in a first position of said collar to condition said pump for purging air from said chamber, and not compressed in a second position of said collar whereby said valve insert member operates as a check valve.

6. A flow system as defined in claim 5 wherein said valve insert member comprises a duckbill-type valve.

7. In a flow system for infusing fluid into the human body, a pressure pump comprising, in combination:
   a pump housing defining a chamber for said pump and an inlet passageway extending to said chamber;
   means including a valve insert member disposed in said passageway for controlling fluid flow through said passageway;
   a flexible support sleeve disposed in axial alignment with said inlet passageway and projecting outwardly from said housing, said valve insert member being disposed within said support sleeve; and
   user-actuable valve control means for selectively deforming said valve insert member to open said insert member whereby trapped air can be purged from said chamber through said inlet passageway.

8. A flow system as defined in claim 7 wherein said valve control means comprise a ring-shaped collar member mounted for rotation about said support sleeve, and a cap member mounted on the free end of said support sleeve for holding said valve insert member and said valve control collar in position thereon.

9. A flow system as defined in claim 8, wherein said cap member includes a hub portion extending within said support sleeve to prevent said sleeve from collapsing.

10. A flow system as defined in claim 1 wherein said valve insert member has a greater opening in said open position than the lumen of the flow system to enable fluid to flow freely through said valve.

11. In a flow system for infusing fluid into the human body, a pressure pump comprising, in combination:
    a pump housing defining a chamber for said pump and including an inlet passageway extending to said chamber;
    means including a duckbill-type valve insert member seated within said passageway for controlling flow through said passageway, said valve insert member having an out-of-round cross-section;
    means including a user-actuated valve control collar having an out-of-round aperture disposed over said valve insert member, said collar being rotatably mounted with respect to said valve insert member whereby said insert member can be radially deformed to condition said valve open for purging air from said pump and allowing free flow of fluid therethrough.

12. In a flow system for infusing fluid into the human body, a pressure pump comprising, in combination:
    a pump housing defining a chamber for said pump and including an inlet passageway extending to said chamber;
    means including a duckbill-type valve insert member seated within said passageway for controlling flow through said passageway, said valve insert member having an out-of-round cross-section;
    a flexible support sleeve disposed in axial alignment with said inlet passageway and projecting outwardly from said housing, said valve insert member being disposed within said sleeve; and
    means including a user-actuated valve control collar having an out-of-round aperture disposed around said valve insert member and said sleeve, said collar also being rotatably mounted with respect to said valve insert member and said sleeve whereby said insert member can be radially deformed to condition said valve open for purging air from said pump and allowing free flow of fluid therethrough.

* * * * *